(12) United States Patent
Chitlaru et al.

(10) Patent No.: US 7,282,352 B2
(45) Date of Patent: Oct. 16, 2007

(54) HOMOGENEITY AND SECRETION OF RECOMBINANT PROTEINS IN MAMMALIAN SYSTEMS

(75) Inventors: Edith Chitlaru, Rehovot (IL); Hagit Amitai, Rehovot (IL); Daniel Helman, Hatzivini (IL)

(73) Assignee: Applied Research Systems ARS Holding N.V., Curacao (NL)

( * ) Notice: Subject to any disclaimer, the term of this patent is extended or adjusted under 35 U.S.C. 154(b) by 366 days.

(21) Appl. No.: 10/858,928

(22) Filed: Jun. 2, 2004

(65) Prior Publication Data

US 2006/0234352 A1   Oct. 19, 2006

Related U.S. Application Data

(63) Continuation-in-part of application No. 10/432,196, filed as application No. PCT/IL01/01125 on Dec. 5, 2001.

(30) Foreign Application Priority Data

Dec. 5, 2000   (IL)   ..................... 140110

(51) Int. Cl.
*C12P 21/06* (2006.01)
*A61K 38/24* (2006.01)

(52) U.S. Cl. ............... 435/69.1; 530/313; 530/398; 530/399; 530/412; 435/320.1; 435/357; 435/360; 435/365; 435/370

(58) Field of Classification Search ............ None
See application file for complete search history.

(56) References Cited

FOREIGN PATENT DOCUMENTS

| AU | 606453 | * | 2/1991 |
|---|---|---|---|
| EP | 0 307 285 A | | 3/1989 |
| EP | 0 211 894 B | | 3/1993 |
| WO | WO 86/04589 | * | 8/1986 |
| WO | WO86/04589 | * | 8/1986 |
| WO | WO98 11206 A | | 3/1998 |
| WO | WO 00 22146 A | | 4/2000 |

OTHER PUBLICATIONS

Olivje et al., Mol. Hum. Reprod., 2, 371-382.*
Olivje et al., Mol. Hum. Reprod., 2, 371-382, 1996.*
Hartman "Human influenza virus hemagglutinin is expressed in monkey cells using simian virus 40 vectors," Proc. Natl. Acad. Sci. USA, 79, 233-237 (1982).
Mazzei "Recombinant Soluble Trimeric CD40 Ligand is Biologically Active," J. Biol. Chem., 270 (13), 7025-7028 (1995).
Nielsen "Identification of prokaryotic and eukaryotic signal peptides and prediction of their cleavage sites," Protein Engineering, 10 (1), 1-6 (1997).
Selden "Human growth hormone as a reporter gene in regulation studies employing transient gene expression," Mollecular and Cellular Biology, 6 (9), 3173-3179 (1986).
Zhao "Formation of mRNA 3' ends in eukaryotes: mechanism, regulation and interrelationships . . . ," Microbiology and Molecular Biology Reviews, 63 (2), 405-445 (1999).
Fanslow "Structural characteristics of CD40 ligand that determine biological function," Seminars in Immunology, 6 (5): 267-278 (Oct. 1994).
Hollenbaugh "The human T cell antigen gp39, a member of the TNF gene family, is a ligand for the CD40 receptor . . . ," EMBO J. 11 (12): 4313-4321 (Dec. 1992).
Kozak "Interpreting cDNA sequences: some insights from studies on translation," Mammalian Genome, 7 (8): 563-574, (Aug. 1996).
Kozak "Initiation of translation in prokaryotes and eukaryotes," Gene, 234 (2): 187-208 (1999).
Sakaguchi "Eukaryotic protein secretion," Curr Opin Biotechnol., 8 (5): 595-601 (Oct. 1997).
Fontes "Bacterial xylanase expression in mammalian cells and transgenic mice," Journal of Biotechnology 72 (1999): 95-101.
Kim "Structural requirements of six naturally occurring isoforms of the IL-18 binding protein to inhibit IL-18," PNAS 97 (3): 1190-1195, 2000.
Morris "Incorporation of an Isoleucine Zipper Motif Enhances the Biological Activity of Soluble CD40L (CD154)," The Journal of Biological Chemistry, 274 (1): 418-423 (1999).
Novick "Interleukin-18 Binding Protein: A Novel Modulator of the Th1 Cytokine Response," Immunity 10: 127-136 (Jan. 1999).
Pecceu "Human interleukin 1 beta fused to the human growth hormone signal peptide is N-glycosylated and secreted by Chinese hamster ovary cells," Gene 97: 253-258 (1999).
Sin "Protective immunity against heterologous challenge with encephalomyocarditis virus by VP1 DNA vaccination . . . ," Vaccine 15 (17/18): 1827-1833 (1997).
Bjorkdahl "Gene transfer of a hybrid interleukin—1 beta gene to B16 mouse melanoma recruits leucocyte . . . ," Cancer Immunol Immunother 44 (5):273-281 (1997).
Komada "Protective Effect of Transfection with Secretable Superoxide Dismutase (SOD) . . . ," Biol Pharm Bull 20 (5):530-536 (1997).
Mountford "Expression and characterization of biologically active ovine FSH from mammalian cell lines," J Mol Endocrinol. Feb. 1994; 12(1):71-83.
Dinarello "Biologic basis for Interleukin-1 in Disease," Blood, 87, 2095-2147, 1996.

* cited by examiner

*Primary Examiner*—Eileen O'Hara
*Assistant Examiner*—Elly-Gerald Stoica
(74) *Attorney, Agent, or Firm*—Browdy & Neimark, PLLC

(57) ABSTRACT

The present invention relates to a method for improving homogeneity and/or secretion of a recombinant protein of interest expressed in mammalian cells by replacing the endogenous signal peptide sequence of the DNA encoding the protein of interest with that of human hGH. Specifically, the present invention relates to a method wherein the protein of interest is a subunit of the follicle stimulating hormone (FSH). The invention also relates to DNA expression vectors containing the sequence encoding such proteins of interest fused to the signal peptide sequence of the hGH and to cells harbouring such vectors.

17 Claims, 4 Drawing Sheets

Figure 1

Exon 1

ATG GCT ACA G

Met Ala Thr G

Intron 1

GTAAGCGCCC CTAAAATCCC TTTGGGCACA ATGTGTCCTG AGGGGAGAGG CAGCGACCTG

TAGATGGGAC GGGGGCACTA ACCCTCAGGT TTGGGGCTTC TGAATGTGAG TATCGCCATG

TAAGCCCAGT ATTTGGCCAA TCTCAGAAAG CTCCTGGTCC CTGGAGGGAT GGAGAGAGAA

AAACAAACAG CTCCTGGAGC AGGGAGAGTG CTGGCCTCTT GCTCTCCGGC TCCCTCTGTT

GCCCTCTGGT TTCTCCCCAG

Exon 2

GC TCC CGG ACG TCC CTG CTC CTG GCT TTT GGC CTG CTC TGC ly Ser Arg Thr Ser Leu Leu Leu Ala Phe Gly Leu Leu Cys signal peptide cleavage site▼

CTG CCC TGG CTT CAA GAG GGC AGT GCC TTC CCA ACC ATT CCC TTA TCC AGG

Leu Pro Trp Leu Gln Glu Gly Ser Ala ▶ Phe Pro Thr Ile Pro Leu Ser Arg

Figure 2

Kozak Concensus          ATG   G
                         +1    +4

Human growth             ATG   G
hormone leader           +1    +4

Figure 3

5'hGH-IL-18BP fusion out primer:  TAT AAGCTT ACC ATG GCT ACA GGC TCC CGG ACG T
                                                    hGH-sp 3' hGH-IL-18BP fusion-in primer:  T GGT CTG CGA GAC AGG TGT GGC ACT GCC CTC TTG
                                          IL-18BP                hGH-sp 5'hGH-IL-18BP fusion-in primer:  CAA GAG GGC AGT GCC ACA CCT GTC TCG CAG ACC A
                                         hGH-sp              IL-18BP 3'hGH-IL-18BP fusion-out primer:  CG GGATCC CTA TTA ACC CTG CTG CTG TGG AC
                                             Stop Stop  IL-18BP

Figure 4

| Cell line | α subunit | β subunit |
|---|---|---|
| Cognate sp on beta (cDNA protoclone 91LP3-3)* | 4% | 27% |
| hGH sp on beta (cDNA protoclone 88LP3-18 ) * | <LOD | <LOD |
| α chain N-terminal sequence: expected APDVQD; truncated DVQD  β chain N-terminal sequence: expected NSXELT; truncated XELT | | |

**\*Edman degradation on immunopurified material**

SEQUENCE LISTING

```
<160> NUMBER OF SEQ ID NOS: 20

<210> SEQ ID NO 1
<211> LENGTH: 338
<212> TYPE: DNA
<213> ORGANISM: Homo sapiens

<400> SEQUENCE: 1
atggctacag gtaagcgccc ctaaaatccc tttgggcaca atgtgtcctg aggggagagg      60
cagcgacctg tagatgggac gggggcacta accctcaggt ttggggcttc tgaatgtgag     120
tatcgccatg taagcccagt atttggccaa tctcagaaag ctcctggtcc ctggagggat    180
ggagagagaa aaacaaacag ctcctggagc agggagagtg ctggcctctt gctctccggc    240
tccctctgtt gccctctggt ttctccccag gctcccggac gtccctgctc ctggcttttg    300
gcctgctctg cctgccctgg cttcaagagg gcagtgcc                            338

<210> SEQ ID NO 2
<211> LENGTH: 26
```

<212> TYPE: PRT
<213> ORGANISM: Homo sapiens

<400> SEQUENCE: 2

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala
            20                  25

<210> SEQ ID NO 3
<211> LENGTH: 4
<212> TYPE: DNA
<213> ORGANISM: Artificial
<220> FEATURE:
<223> OTHER INFORMATION: Nucleotides 1-4  encoding hGH signal peptide

<400> SEQUENCE: 3 atgg                                                                    4

<210> SEQ ID NO 4
<211> LENGTH: 31
<212> TYPE: DNA
<213> ORGANISM: Artificial
<220> FEATURE:
<223> OTHER INFORMATION: forward PCR primer comprising a SalI
      restriction site and the first 21 nucleotides encoding hGHsp

<400> SEQUENCE: 4
acgcgttcga cgccaccatg gctcccggac g                                     31

<210> SEQ ID NO 5
<211> LENGTH: 29
<212> TYPE: DNA
<213> ORGANISM: Artificial
<220> FEATURE:
<223> OTHER INFORMATION: reverse PCR primer comprising the last 18
      nucleotides of IL-18BP, two stop codons and a Bam HI restriction
      site

<400> SEQUENCE: 5
cgggatcctc attaccctg ctgctgtgg                                         29

<210> SEQ ID NO 6
<211> LENGTH: 34
<212> TYPE: DNA
<213> ORGANISM: Artificial
<220> FEATURE:
<223> OTHER INFORMATION: 5' primer for amplifying hGHsp from pXGH5

<400> SEQUENCE: 6
tataagctta ccatggctac aggctcccgg acgt                                  34

<210> SEQ ID NO 7
<211> LENGTH: 34
<212> TYPE: DNA
<213> ORGANISM: Artificial
<220> FEATURE:
<223> OTHER INFORMATION: 3' primer for amplifying hGHsp from pXGH5

<400> SEQUENCE: 7
tggtctgcga gacaggtgtg gcactgccct cttg                                  34

<210> SEQ ID NO 8
<211> LENGTH: 34
<212> TYPE: DNA
<213> ORGANISM: Artificial

```
<220> FEATURE:
<223> OTHER INFORMATION: 5' primer for amplifying mature IL-18BP

<400> SEQUENCE: 8
caagagggca gtgccacacc tgtctcgcag acca                               34

<210> SEQ ID NO 9
<211> LENGTH: 31
<212> TYPE: DNA
<213> ORGANISM: Artificial
<220> FEATURE:
<223> OTHER INFORMATION: 3' primer for amplifying mature IL-18BP

<400> SEQUENCE: 9
cgggatccct attaaccctg ctgctgtgga c                                  31

<210> SEQ ID NO 10
<211> LENGTH: 15
<212> TYPE: PRT
<213> ORGANISM: Artificial
<220> FEATURE:
<223> OTHER INFORMATION: N-terminal amino acid sequence of IL18-BP
      exprssed with hGHsp

<400> SEQUENCE: 10

Thr Pro Val Ser Gln Thr Thr Thr Ala Ala Thr Ala Ser Val Arg
1               5                  10                  15

<210> SEQ ID NO 11
<211> LENGTH: 48
<212> TYPE: DNA
<213> ORGANISM: Artificial
<220> FEATURE:
<223> OTHER INFORMATION: 5' PCR primer for amplifying fragment
      encoding hGHsp from pSIL18BP

<400> SEQUENCE: 11
aatccattta aatcgccacc atggctacag gctcccggac ctccctgc                48

<210> SEQ ID NO 12
<211> LENGTH: 38
<212> TYPE: DNA
<213> ORGANISM: Artificial
<220> FEATURE:
<223> OTHER INFORMATION: 3' PCR primer for amplifying fragment
      encoding hGHsp from pSIL18BP

<400> SEQUENCE: 12
ttggtcagct cacagctatt ggcactgccc tcttgaag                           38

<210> SEQ ID NO 13
<211> LENGTH: 44
<212> TYPE: DNA
<213> ORGANISM: Artificial
<220> FEATURE:
<223> OTHER INFORMATION: 5' PCR primer for amplifying fragment
      encoding mature FSH beta

<400> SEQUENCE: 13
tggcttcaag agggcagtgc caatagctgt gagctgacca acat                    44

<210> SEQ ID NO 14
<211> LENGTH: 34
<212> TYPE: DNA
<213> ORGANISM: Artificial
<220> FEATURE:
```

```
<223> OTHER INFORMATION: 3' PCR primer for amplifying fragment
      encoding mature FSH beta

<400> SEQUENCE: 14
ccgctcgagg tttattctttt catttcacca aagg                              34

<210> SEQ ID NO 15
<211> LENGTH: 41
<212> TYPE: DNA
<213> ORGANISM: Artificial
<220> FEATURE:
<223> OTHER INFORMATION: 5' PCR primer for amplifying vector for
      expression of FSH beta

<400> SEQUENCE: 15
aatccattta aatcgccacc atgaagacac tccagttttt c                       41

<210> SEQ ID NO 16
<211> LENGTH: 34
<212> TYPE: DNA
<213> ORGANISM: Artificial
<220> FEATURE:
<223> OTHER INFORMATION: 3' PCR primer for amplifying vector for
      expression of FSH beta

<400> SEQUENCE: 16
ccgctcgagg tttattctttt catttcacca aagg                              34

<210> SEQ ID NO 17
<211> LENGTH: 6
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: undetermined

<400> SEQUENCE: 17

Asn Ser Xaa Glu Leu Thr
1               5

<210> SEQ ID NO 18
<211> LENGTH: 6
<212> TYPE: PRT
<213> ORGANISM: Homo sapiens

<400> SEQUENCE: 18

Ala Pro Asp Val Gln Asp
1               5

<210> SEQ ID NO 19
<211> LENGTH: 4
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: undetermined

<400> SEQUENCE: 19

Xaa Glu Leu Thr
1

<210> SEQ ID NO 20
<211> LENGTH: 4
<212> TYPE: PRT
<213> ORGANISM: Homo sapiens
```

```
<400> SEQUENCE: 20

Asp Val Gln Asp
1
```

US 7,282,352 B2

HOMOGENEITY AND SECRETION OF RECOMBINANT PROTEINS IN MAMMALIAN SYSTEMS

CROSS REFERENCE TO RELATED APPLICATIONS

The present application is a continuation-in-part of U.S. application Ser. No. 10/432,196 filed May 20, 2003, which is a national stage application claiming priority to PCT/IL01/01125 filed Dec. 5, 2001, which claims priority of Israel application number 140110 filed Dec. 5, 2000, incorporated herein by reference in their entirety.

FIELD OF THE INVENTION

The present invention relates to a method for improving homogeneity and/or secretion of a recombinant protein of interest expressed in mammalian cells by replacing the endogenous signal peptide sequence of the DNA encoding the protein of interest with that of human hGH. The invention also relates to DNA expression vectors containing the sequence encoding such proteins fused to the signal peptide sequence of the hGH and to cells harbouring such vectors.

BACKGROUND OF THE INVENTION

Protein secretion is one of the most important issues of protein production in the field of biotechnology. This process is composed of the following steps: first, translocation across the endoplasmic reticulum (ER) membrane; second N-glycosylation and folding in the ER lumen; third, exit from the ER; fourth, modifications in the Golgi apparatus; and finally release from the secretory granules to the extracellular space (Sakaguchi 1997). Whether or not a protein is secreted from the cells mainly depends on whether it can be translocated across the membrane and whether it can be correctly folded in the ER lumen. Membrane translocation is obligatorily coupled in mammalian cells. After membrane translocation, the nascent peptides are released into the lumenal space and folded with the assistance of various chaperones and folding enzymes. Wrongly folded proteins are trapped within the ER and thus cannot proceed towards the secretory compartments. In biotechnological processes in which massive protein expression occurs, secretion can represent a bottleneck and limit the rate of expression.

Signal peptides or leader sequences, are located at the amino terminus of nascent polypeptides. They target proteins to the secretory pathway and are cleaved from the nascent chain once translocated in the reticulum endoplasmatic membrane.

The signal peptide consists of three regions: an amino-terminal polar region (N region), where positive charged aminoacid residues are frequently observed; a central hydrophobic region (H region) of more than 7-8 hydrophobic amino acid residues; and a carboxy-terminal region (C region) that includes the signal peptide cleavage site (Sakaguchi 1997). The eukaryotic H regions are dominated by Leu with some occurrence of Val, Ala, Phe and Ile. The cleavage of the signal peptide from the mature protein occurs at a specific site and the cleavage specificity resides in the last residue of the signal sequence (Nielsen et al. 1997). Close to the cleavage site −3 and −1 alanine is more predominant. This site confers processing specificity. No further specific patterns in the first few positions of the mature protein can be seen in eukaryotic organisms (Nielsen et al 1997). Therefore a "bad" signal peptide can promote more than one specific cleavage resulting in non-homogenous expression of the protein; i.e. the protein will be expressed with different N-terminal aminoacids.

Since many proteins are regulated under physiological conditions the use of natural regulatory signals for overexpression in mammalian systems is not desirable. For example, in such systems efficient promoters such as CMV and SV40 are used to control expression of recombinant proteins of interest. Similarly, the use of effective signal peptides such as SV40 and hGH poly A to overexpress recombinant secreted proteins instead of their endogenous counterparts would be advantageous.

The signal peptide of the human growth hormone (hGH) has been described to be effective in targeting the secretion of intracellular, membrane bound proteins and proteins secreted by different mechanisms than those governed by signal peptides.

For example, WO26562 describes the secretion of the intracellular protein icIL-1ra-II by fusion of the signal peptide of hGH to the sequence of the icIL-1ra-II. The invention relates to a process for the recombinant expression of a protein having the amino acid sequence of natural icIL-1ra-II in a recombinant cell expression system through use of a vector which is a fusion of the signal peptide of a human secretory protein, preferably the 26 amino acid signal peptide of hGH, fused in proper reading frame with the DNA encoding icIL-1ra-Il. The process comprises producing an expression vector containing DNA encoding icIL-1ra-II, either in the form of cDNA or genomic DNA, fused in proper reading frame with DNA encoding the selected signal peptide (SEQ ID NO:1), preferably the 26 amino acid hGH signal peptide (FIG. 1 SEQ ID NO:2). The expression vector is then inserted into an appropriate expression host, such as CHO cells. The transformed host cells are then cultured in a manner, which causes the expression vector to express its encoded protein, and the expressed and secreted icIL-1ra-II protein is then collected and purified from the culture medium.

Morris at al. (1999) describes the use of hGH signal peptide for the secretion of the protein CDL40L, which exists in nature predominantly as a membrane-anchored molecule. Several reports have shown that the soluble form of CD40L is biologically active (Fanslow et al. 1994, Hollenbaugh et al. 1992 and Mazzei et al. 1995). To use CD40L as a potential therapeutic, optimisation of soluble forms of this molecule have been developed. In this work, the activity of soluble forms of CD40L, and the activity of the soluble multimerized CD40L TNF homologous region, have been compared. The soluble forms of CD40L have been prepared by fusion of the entire extracellular domain of human CD40L or the CD40L region homologous to TNF sequence to the signal peptide sequence of hGH. The multimerized form of the CD40L has been prepared by fusion to an isoleucine zipper (IZ). The results showed that multimerization increases the activity of soluble CD40L.

Pecceu et al (1991) describes the use of the hGH signal peptide to express and secrete the mature form of IL-1β. In the body, after synthesis, proIL-1β remains primarily cytosolic until it is cleaved and transported out of the cells. Examination of the sequence reveals the absence of a classical N-terminal or internal hydrophobic signal peptide. Release of mature IL-1β appears to be linked to processing at the aspartic acid-alanine peptide cleavage by the converting enzyme (ICE) (Dinarello 1996). Although ICE is constitutively expressed in most cells, not all cells process proIL-1β and secrete mature IL-1β. Therefore secretion of mature IL-1β is cell dependent. Pecceu discloses the use a recombinant vector containing only the DNA encoding the mature form of IL-1β, without any signal peptide and a vector containing the DNA encoding the mature form of IL-1β joined to hGH signal peptide. The results show that only 52% of the protein are secreted using the first construct, while using the construct with hGH signal peptide results in 97% secretion.

The first ATG codon for initiation of translation has to be identified by the transcriptional machinery. An ATG codon in a very weak context is not likely to be the start site for translation. The optimal context for initiation of translation in vertebral mRNAs is a G residue following the ATG codon (position +4 in the coding region) and a purine, preferable A, three nucleotides upstream (−3 in the noncoding region) this consensus sequence has been designated Kozak sequence (Kozak 1996, 1999). Messenger RNA in which the first ATG codon lacks the preferred nucleotides in both of these key flanking positions (a "bad" or non optimal Kozak sequence) have the special property of initiating translation at the first and second ATG codons, thereby producing two proteins from one RNA. The ATG in the initiation site of hGH signal peptide is followed by G (in position +3) required for obtaining an optimal Kozak sequence (FIGS. 1 and 2 SEQ ID NO:3), which ensures the start of translation at the first ATG site only and homogeneity of the product.

IL-18 binding protein (IL18-BP) was affinity purified from human urine using IL-18, sequenced and cloned. IL-18BP was found to abolish in vitro the activity of the pro-inflammatory cytokine IL-18. (Novick et al. 1999). The DNA encodes a signal peptide at its N-terminal portion. Part of the Kozak sequence encoded inside the signal peptide is not of the appropriate context.

| IL-18BP leader | |
|---|---|
| ATG | A |
| +1 | +4 |
| ATG | G |
| Kozak Concensus | |
| +1 | +4 |
| Human growth hormone leader | |
| +1 | +4 |

Many naturally occurring proteins and enzymes are multimeric. Examples include hemoglobin, antibody, thyrotropin (TSH), fertility hormones such as follicle stimulating hormone (FSH), luteinizing hormone (LH) and human choriogonadotropin (HCG). The subunits of a multimeric protein may be identical, homologous or totally dissimilar and dedicated to different tasks.

Follicle stimulating hormone is known to be useful in the treatment of infertility. FSH is comprised of two polypeptide subunits, alpha and beta. Preparations containing this hormone have been employed to assist in effecting pregnancy using both in-vivo and in-vitro techniques. Human FSH has been isolated from human pituitary glands and from postmenopausal urine. More recently, it has been produced using recombinant DNA techniques (EP0211894B).

Mountford et al. described the purification and characterization of ovine FSH secreted by CHO cell lines stably transfected with cDNA constructs encoding the alpha and beta sub-units of this hormone. Replacement of the 5' untranslated and signal peptide-coding sequence with those from an ovine growth hormone resulted in a mixed population of beta sub-unit polypeptides derived from two cleavage sites.

Thus, new methods for improving homogeneity of production of recombinant proteins comprising more than one polypeptide subunit are needed.

It has been found in accordance with the present invention that mammalian engineered cells harbouring DNA encoding human FSH, and in the DNA the endogenous human FSH signal peptide was replaced with the human growth hormone signal peptide, produced more homogenous FSH.

SUMMARY OF THE INVENTION

The invention provides an improved method for production of homogeneous recombinant protein of interest expressed in different mammalian systems and or effective secretion thereof comprising replacing the endogenous signal peptide sequence of the DNA encoding the protein of interest with that of hGH.

The invention also provides an expression vector for improving homogeneity and/or secretion of a recombinant protein of interest expressed in a mammalian system comprising the signal peptide sequence of the hGH joined to the DNA encoding the protein of interest.

In one aspect, the present invention provides said vector, which encodes the optimal Kozak sequence ensuring translation from one initiation codon only. Part of such a sequence is included in the coding for the hGH signal peptide, ensuring accurate cleavage of the signal peptide from the mature protein.

In one embodiment of the present invention the vector includes the gene encoding IL-18BP. Such a vector allows the production of homogeneous IL-18BP (starting with Thr-Pro-Val).

The invention also provides a protein of interest produced with the said vector and by the said method, such as IL-18BP.

In another aspect, the invention provides cells capable of growing in serum free medium and able to produce at least 4 picogram IL-18B/cell/24 hours, preferably at least 11.8 picogram/cell/24 hours and most preferably about 12 picograms/cell/24 hours.

The invention also relates to a method for improving the homogeneity of production of a recombinant protein of interest composed of more than one subunit in a mammalian cell, comprising the step of substituting the endogenous signal peptide of at least one of the subunits with an amino acid sequence comprising the signal peptide of human growth hormone (hGH).

In a preferred embodiment, only the endogenous signal peptide of one of the subunits is substituted with an amino acid sequence comprising the signal peptide of hGH.

In one embodiment, examples for the protein of interest that are produced with the method of invention are fertility hormones such as luteinizing hormone (LH) and human choriogonadotropin (HCG) and more preferably, FSH. In particular, the signal peptide of the beta subunit of fertility hormones can preferably be replaced with an amino acid sequence comprising the signal peptide of the hGH.

In one aspect, examples of mammalian cell for using according to the invention are 3T3 cells, COS cells, human osteosarcoma cells, MRC-5 cells, BHK cells, VERO cells, CHO cells, rCHO-tPA cells, rCHO-Hep B Surface Antigen cells, HEK 293 cells, rHEK 293 cells, rC127-Hep B Surface Antigen cells, Normal Human fibroblast cells, Stroma cells, Hepatocytes cells, PER.C6 cells and human permanent amniocytic cells. In a more preferred embodiment, the mammalian cells is CHO.

In another aspect, the invention provides an expression vector for improving homogeneity of production of a recombinant protein of interest composed of more than one subunit, comprising the DNA sequence of one or more subunit, and the DNA sequence of at least one subunit's endogenous signal peptide is replaced with the DNA encoding the sequence of the hGH signal peptide. Examples for protein of interest that are produced with the expression vector of the invention are thyrotropin (TSH), fertility hormones such as luteinizing hormone (LH) and human choriogonadotropin (HCG) and more preferably, FSH. In particular, the signal peptide of the beta subunit of fertility hormones can be replaced with an amino acid sequence comprising the signal peptide of hGH. In addition, the expression vector can contain the beta subunit and the alpha subunit as well.

In a further embodiment, the invention provides a cell producing a protein of interest composed of more than one subunit comprising the vector of the invention.

Preferably, the cell of the invention produced a protein of interest such as TSH, HCG, LH and most preferably FSH.

In a further preferred embodiment, the cell of the invention comprises a vector encoding the sequence of the beta subunit and a vector encoding the sequence of the alpha subunit, wherein the endogenous signal peptide of either one or both subunits is/are replaced with that of the hGH signal peptide.

In a preferred embodiment of the invention, the cell of the invention produces FSH in the range of 2 to 20 picogram/cell/24 hours, 2 to 10 picogram/cell/24 hours, 4 to 8 picogram/cell/24 hours and/or at about 4 picogram FSH/cell/24 hours.

In a more preferred embodiment, the cell of the invention is capable of growing in serum free medium.

In a further embodiment, the invention provides a method for producing a recombinant protein of interest, composed of more than one subunit, comprising the step of growing a cell of the invention and isolating the protein produced. Examples of recombinant proteins of interest produced by the method of the invention are TSH, HCG, LH and preferably FSH.

The invention further provides a recombinant protein of interest composed of more than one subunit, such as TSH, HCG, LH and preferably FSH, obtainable by the method of production according to the invention.

In a further preferred embodiment, the invention provides a pharmaceutical composition comprising a protein of interest composed of more than one subunit, such as TSH, HCG, LH and preferably FSH, produced according to the method of the invention.

BRIEF DESCRIPTION OF THE FIGURES

FIG. 1 shows the genomic sequence encoding the hGH signal peptide and translated amino acid sequence.

FIG. 2 shows the Kozak sequence present in the consensus and in the hGH signal peptide.

FIG. 3 describes the primers used for the fusion of hGH signal peptide (without its intron) sequence with the IL-18BP sequence.

FIG. 4 shows the N terminal sequences of FSH subunits alpha and beta in cells utilizing the hGH signal peptide versus the endogenous signal peptide for secretion. (LOD=limit of detection).

DETAILED DESCRIPTION OF THE INVENTION

The present invention relates to the production and secretion of homogenous recombinant protein by using the signal peptide sequence of the hGH instead of the natural or endogenous signal peptide sequence. The invention also provides an expression vector containing the DNA encoding the protein of interest, either in the form of cDNA or genomic DNA, fused in proper reading frame with the DNA encoding the hGH signal peptide. The expression vector is then inserted into an appropriate expression host, i.e. mammalian cells. The transformed host cells are then cultured in a manner, which causes the expression vector to express its encoded protein, and the expressed and secreted protein is then isolated and purified. The expression of the protein of interest may be stable or transient.

While CHO cells are the preferred host cells, other mammalian cells may be used, such as 3T3 cells, COS cells, human osteosarcoma cells, MRC-5 cells, BHK cells, VERO cells, CHO cells, rCHO-tPA cells, RCHO-Hep B Surface Antigen cells, HEK 293 cells, rHEK 293 cells, rC127-Hep B Surface Antigen cells, Normal Human fibroblast cells, Stroma cells, Hepatocytes cells, PER.C6 cells and human permanent amniocytic cells. Those of ordinary skill in the art are well aware of the techniques of creating expression vectors, inserting them into expression systems and selecting clones, which express the desired protein, including amplification techniques.

As will be appreciated by those skilled in the art, the types of promoters used to control transcription of the recombinant proteins may be any of those, which are functional in the host cells. Examples of promoters functional in mammalian cells include the SV40 early promoter, adenovirus major late promoter, herpes simplex (HSV) thymidine kinase promoter, rous sarcoma (RSV) LTR promoter, human cytomegalovirus (CMV) immediate early promoter, mouse mammary tumor virus (MMTV) LTR promoter, interferon-β promoter, heat shock protein 70 (hsp 70) promoter, as well as many others well known in the art. These promoters may be either constitutive or regulatable. Constitutive promoters are preferred because an extra treatment step, such as temperature shift, addition of chemical agents or inducers, etc., is not required for expression from constitutive promoters. It has been shown in one embodiment that higher productivity can be obtained by controlling IL-18BP expression with the CMV promoter as compared to the SV40 promoter.

In mammalian cells, three elements define the core polyadenylation signal i.e. the highly conserved hexanucleotide AAUAAA found 10 to 30 nucleotides upstream of the cleavage site, a less highly conserved U-rich or GU-rich element located downstream of the cleavage site, and the cleavage site itself, which becomes the point of poly(A) addition and is thus generally referred to as the poly(A) site (Zhao et al. 1999). Additional sequences outside of this core recruit regulatory factors or maintain the core signal in an open and accessible structure. Different expression vectors for heterologous expression have been designed to contain efficient polyadenylation signals such as SV40 and hGH polyadenylation signals. In a preferred embodiment IL-18BP is produced using the human growth hormone polyadenylation signal.

In particular, the present invention relates to an expression vector which contains the IL-18BP DNA fused to the DNA encoding the signal peptide of hGH, and to host cells transfected with such an expression vector.

The DNA sequence of the hGH signal peptide used, may be either the genomic sequence including the intron (FIG. 1 SEQ ID NO:1) or the cDNA sequence of the signal peptide excluding the intron.

In accordance with the present invention it is possible to express, IL-18BP and other secreted proteins homogeneously and effectively in a mammalian expression system using the signal peptide of hGH.

In addition, the invention relates to mammalian cells which express and efficiently secrete homogenous recombinant proteins using the hGH signal peptide. In another aspect, the invention relates to cells which efficiently secrete homologous recombinant proteins, according to the invention, that are capable of being grown and produced in serum free medium (SFM). More specifically, in a preferred embodiment cells, according to the invention, were shown to produce between 4 and 11.8, and also about 12 picogram IL-18BP/cell/24 hours in both serum and serum free conditions.

The invention also relates to proteins of interest prepared according to the method herein described. In another aspect, the invention relates to pharmaceutical compositions comprising proteins of interest, such as IL-18BP produced in such an expression system, optionally together with a pharmaceutically acceptable excipient.

In a further embodiment, the invention relates to a method for improving the homogeneity of production of a recombinant protein of interest composed of more than one subunit such from human or animal origin, in a mammalian cell, the method comprises the step of substituting the endogenous signal peptide of at least one of the subunits with an amino acid sequence of the signal peptide of the human growth hormone (hGH). Fertility hormones have two sub units, one alpha and one beta, the alpha subunit is common to the fertility hormones LH, leuteinizing hormone (LH) and FSH.

Examples protein of interest comprising more than one subunit include, but are not limited, to hemoglobin, antibody, thyrotropin (TSH), fertility hormones such as follicle stimulating hormone (FSH), luteinizing hormone (LH) and human choriogonadotropin (HCG).

A protein subunit or subunit protein is a single protein molecule that assembles (or "coassembles") with other protein molecules to form a multimeric or oligomeric protein.

The present invention relates to methods of improving N-terminal homogeneity of a protein of interest composed of more than one subunits, resulting in secretion of more than 75%, 80%, 90%, 98% or 99% of each of the subunits of the protein of interest, having a correct N-terminal amino acid sequence.

The invention is based on the surprising findings that the human FSH, composed of the alpha and beta subunits, is more homogeneously produced when instead of the cognate signal peptide of the beta FSH subunit, the human GH signal peptide is used (Example 4 and 5).

In accordance with the invention, the endogenous signal peptide of at least one of the subunits, may be substituted with the signal peptide of the hGH. In a preferred embodiment of the invention, the signal peptide of the FSH beta subunit is the only signal peptide substituted.

The present invention also relates to an expression vector which can be used for improving homogeneity of production of a recombinant protein of interest composed of more than one subunit. The vector may comprise the DNA sequence of one or more subunits, and the endogenous signal peptide of at least one subunit is substituted with the hGH signal peptide. In a preferred embodiment of the invention the expression vector comprises the DNA sequence of the FSH subunit beta and the endogenous signal peptide of the FSH subunit beta substituted with the DNA sequence of the hGH signal peptide.

In another embodiment, the expression vector may comprise the DNA sequences encoding all the subunits of the protein of interest, and at least one of the DNA subunits having the endogenous signal peptide substituted with the hGH signal peptide.

In addition, the invention relates also to a cell producing homogenous protein of interest composed of more than one subunits. The cell of the invention harbors one or more expression vectors comprising the DNA sequence of one, more than one, or of all the subunits of said protein of interest, wherein the endogenous signal peptide of at least one of the subunits of the protein of interest is substituted with the DNA of the hGH signal peptide.

In a preferred embodiment, the cell of the invention contains more than one expression vector, such as one vector for one subunit. For example, for the expression of FSH, a cell may contain one expression vector for the alpha subunit and another expression vector for the beta subunit, and at least the endogenous signal peptide of one of the sub units, preferably the beta subunit, is replaced with that of the hGH signal peptide.

In a further embodiment, the cells of the invention are capable of producing FSH in the range of 2-20 picogram/cell/24 hours, 2-10 picogram FSH/cell/24 hours, 4-8 picogram FSH/cell/24 hours and/or at about 4 picogram FSH/cell/24 hours, in serum or in serum free medium.

Preferably, the cell of the invention is CHO. More preferably the cell of the invention is CHO and capable of growing in serum free medium.

In a further embodiment, the invention relates to a method for producing a recombinant protein of interest, composed of more than one subunit, such as for example TSH, HCG, FSH and LH, comprising the step of growing said cell of the invention, and isolating the protein produced. In a preferred embodiment, the recombinant protein of interest is FSH.

The invention further relates to recombinant proteins of interest prepared according to the method herein described. Preferably, said protein is selected from the group consisting of HCG, LH and preferably, FSH.

In another aspect, the invention relates to pharmaceutical compositions comprising proteins of interest, such as FSH prepared according to the method herein, optionally together with a pharmaceutically acceptable excipient.

The invention will be now illustrated by the following non-limiting examples.

EXAMPLES

Example 1

Establishment of the IL-18BP Producing Clone S10-21

The DNA of the natural signal peptide of the IL-18BP protein encodes for a non-optimal Kozak sequence because the +4 is A and not G therefore it was replaced by hGH signal peptide which exhibits an optimal Kozak sequence (FIG. 2 SEQ ID NO:3). The DNA fragment encoding the hGH signal peptide fused to the IL-18BP protein was introduced in a mammalian expression vector under the control of the SV-40 promoter and polyadenylation signal.

For the preparation of the expression vector, hGH signal peptide (without its intron, see FIG. 1) was fused directly to the cDNA coding for the mature hIL-18BP protein (variant A, accession number AF110799 in the NCBI public databases) by PCR (FIG. 3 describes the primers used).

The hGH signal peptide (without its intron) was amplified by PCR using pXGH5 (Selden et al. 1986) as a template and two primers, a) a primer containing sequences from the beginning of the hGHsp (5'hGH-IL-18BP fusion out primer SEQ ID NO:6) and b) a primer encoding sequences from the end of the hGHsp and sequences coding the first 19 nucleotides of the mature IL-18BP cDNA (3' hGH-IL-18BP fusion-in primer SEQ ID NO:7).

The cDNA coding for the mature IL-18BP was amplified by PCR using a plasmid encoding the IL-18BP cDNA, as a template and two primers, a) a primer coding overlapping sequences to the hGH signal peptide end and the beginning of the mature IL-18BP cDNA (the 5'hGH-IL-18BP fusion-in primer SEQ ID NO:8) and b) a primer containing the end of the IL-18BP cDNA sequence (the 3'hGH-IL-18BP fusion-out primer SEQ ID NO:9).

The fragments resulting from the above PCR amplification were fused in a third PCR, by annealing of the overlapping sequences present in both fragments and using two primers a) the primer 5'hGH-IL-18BP fusion out, and b) the primer 3'hGH-IL-18BP fusion-out primers.

The resulting PCR DNA fragment was cloned into the mammalian expression vector pSVE3 (Hartman et al. 1982) encoding the commonly used regulatory signals, the SV40 promoter and SV40 polyA signal (the 5' and 3' fusion out primers contained also specific restriction sites sequences needed for cloning).

The constructed plasmid (PSIL18BP) was used for transfecting CHO (DHFR-) cells together with a plasmid containing the mouse DHFR gene as a selective marker.

Individual isolates were isolated in selective medium and assayed for IL-18BP production by an ELISA assay.

Several rounds of gene amplification with increasing MTX concentrations were carried out. After amplification, clones were isolated by limiting dilution. After subcloning the selected clone S10-21 showed a specific and stable productivity of 1 picogram/cell/24 hours.

Example 2

Establishment of the IL-18BP producing clone 22C2-11

The DNA of the natural signal peptide of the IL-18BP protein encodes for a non-optimal Kozak sequence because the +4 is A and not G therefore it was replaced by hGH signal peptide which exhibits an optimal Kozak sequence (FIG. 2 SEQ ID NO:3). The DNA fragment encoding the hGH signal peptide fused to the IL-18BP protein was introduced in a mammalian expression vector under the control of the CMV promoter and the human growth hormone polyadenylation signal.

For the preparation of the expression vector, the DNA encoding the hGH signal peptide (without its intron see FIG. 1) was fused directly to the cDNA coding for the mature hIL-18BP protein (variant A accession number AF 110799) by PCR using the expression vector generated in example 1 (PSIL18BP) as a template and two primers, a) the forward primer ACGCGTTCGACGCCACCATGGCTCCCGGACG (SEQ ID NO:4) comprising a SalI restriction site, and the first 21 bases encoding the cDNA hGH signal peptide and b) the reverse primer CGGGATCCTCATTAACCCTGCT-GCTGTGG (SEQ ID NO:5) comprising the last 18 bases of IL-18BP, two stop codons and a Bam HI restriction site.

The resulting PCR DNA fragment was inserted into a mammalian expression vector, using known molecular genetic manipulations, wherein the mammalian vector comprise the commonly used regulatory signals to be used to express IL-18BP: the CMV promoter and hGH polyA signal (Ausubel et al., Current Protocols in Molecular Biology, Greene Publications and *Wiley Interscience*, New York, N.Y., 1987-1995; Sambrook et al., Molecular Cloning: A Laboratory Manual, Cold Spring Harbor Laboratory, Cold Spring Harbor, N.Y., 1989).

The constructed plasmid (pCMV-IL18 bp2) was used for transfecting CHO (DHFR-) cells together with a plasmid containing the mouse DHFR gene as a selective marker.

Individual isolates were isolated in selective medium and assayed for IL-18BP production by an ELISA assay.

Several rounds of gene amplification with increasing MTX concentrations were carried out (up to 1000 nM) on selected high producer isolates. Following amplification the MTX was removed and high producer clones were isolated by limiting dilution and screening the activity. After cloning the selected clone 22C2-11 showed high specific productivity of 4 picogram/cell/24 hours and stability in serum at 37° C. The 22C2-11 clone was found to grow and produce IL-18BP also under serum free conditions. The productivity of the clone 22C2-11 was tested at lower temperatures. At 32-33° C., both in serum and serum free conditions, the productivity was found to increase to 11.8 picogram IL-18BP/cell/24 hours.

These results indicate that using a construct controlling expression from the CMV promoter and hGH ployA signal allowed increased IL-18BP expression as compared to the expression levels controlled from the SV40 promoter and SV40 poly A signal (example 1).

Example 3

Purification and N-Terminal Analysis of the IL-18BP Produced

The IL-18BP in the supernatant of all the producing cells (S10-21 and 22C2-11 examples 1 and 2 respectively) was purified by immunoaffinity chromatography. N-terminal analysis of the IL18-BP expressed with the signal peptide of hGH, revealed only the correct species of IL-18B with the following N-terminal amino acid sequence T P V S Q T T T A A T A S V R (SEQ ID NO:10). These results show that IL-18BP is homogeneously produced, from different expression vectors, by using the hGH signal peptide in which, in contrast to the IL-18BP natural signal peptide, the Kozak signal is of optimal context.

Example 4

Establishment of Cells Producing Human FSH

For preparing CHO cells producing human FSH, the cells were co-transfected with two expression vectors, one for the expression of FSH alpha subunit and another for the expression of FSH beta subunit.

In the expression vector for the FSH beta subunit, the DNA sequence encoding the natural signal peptide of the FSH beta subunit was replaced by the sequence encoding the hGH signal peptide, which exhibits an optimal Kozak sequence (FIG. 2 SEQ ID NO: 3).

For the preparation of the DNA fragment encoding the hGH signal peptide fused to the FSH beta, the hGH signal peptide cDNA (FIG. 1) was fused directly to the cDNA coding for the mature FSH beta protein (accession number AAA52475 in the NCBI public databases) by PCR.

For the PCR, the nucleotide sequence encoding the hGH signal peptide (without its intron) was amplified by using pSIL18BP (see Example 1) as a template and two primers, a) a primer containing nucleotide sequences from the beginning of the hGHsp (5'fusion out primer SEQ ID NO: 11 AATCCATTTAAATCGCCACCATGGCTA-CAGGCTCCCGGACCTCCCTGC) and b) a primer encoding nucleotide sequences from the end of the hGHsp and nucleotide sequences encoding the first 20 nucleotides of the mature FSH beta cDNA (3' fusion-in primer TTGGT-CAGCTCACAGCTATTGGCACTGCCCTCTTGAAG SEQ ID NO: 12).

The cDNA sequence coding for the mature FSH beta was amplified by PCR using a plasmid encoding the FSH beta cDNA, as a template and two primers, a) a primer containing an overlapping nucleotide sequence to the hGH signal peptide end and a nucleotide sequence encoding the beginning of the mature FSH beta cDNA (the 5' fusion-in primer SEQ ID NO: 13

TGGCTTCAAGAGGGCAGTGCCAATAGCT-GTGAGCTGACCAACAT), and b) a primer containing a nucleotide sequence of the end of the FSH beta cDNA (the 3' beta fusion-out primer SEQ ID NO: 14

CCGCTCGAGGTTTATTCTTTCATTTCACCAAAGG).

The fragments resulting from the above PCR amplification were fused in a third PCR, by annealing of the overlapping sequences present in both fragments and using the two fusion out primers a) the primer 5' fusion out (SEQ ID NO: 11), and b) the primer 3'beta fusion-out primer (SEQ ID NO: 14). The 5' and 3' fusion out primers contained also specific restriction sites sequences needed for insertion into a mammalian expression vector.

After signal peptide replacement, the DNA fragment encoding the hGH signal peptide fused to the FSH beta was introduced in a mammalian expression vector under the control of the CMV promoter and hGH polyadenylation signal, and comprising the puromycin resistance. The resulting vector was designated pCMV-P-hGHspFSHbeta.

In parallel, a vector for the expression of the FSH beta subunit with the endogenous signal peptide was also prepared.

The following primers were employed:

```
5' PCR primer:
AATCCATTTAAATCGCCACCATGAAGACACTCCAGTTTTTC    (SEQ ID
                                              NO: 15)

3' PCR primer:
CCGCTCGAGGTTTATTCTTTCATTTCACCAAAGG    (SEQ ID NO: 16)
```

The resulting PCR DNA fragment inserted into the same mammalian expression vector as above and was designated pCMV-P-enspFSHbeta.

Each of the constructed vectors either comprising the sequence for the beta FSH subunit with the hGH signal peptide or comprising the endogenous FSH beta signal peptide, pCMV-P-hGHspFSHbeta and pCMV-P-enspFSHbeta respectively, was used for transfecting CHO DUKX-B11 (DHFR−) cells together with a plasmid containing the cDNA sequence of the FSH alpha subunit (with the cognate signal peptide) and the mouse DHFR gene as a selective marker (Ausubel et al., Current Protocols in Molecular Biology, Greene Publications *and Wiley Interscience*, New York, N.Y., 1987-1995; Sambrook et al., Molecular Cloning: A Laboratory Manual, Cold Spring Harbor Laboratory, Cold Spring Harbor, N.Y., 1989).

Pools of transfected cells were isolated in selective medium and assayed for FSH production by a specific ELISA assay (Example 6). Limiting dilution was performed on high producer selected pools and protoclons were isolated. Following two further rounds of cloning, high subclones were isolated.

The medium used for selection of FSH cDNA pools and protoclons was:

Dulbecco's Modified Eagle Medium (DMEM) supplemented with 10% Dialyzed FBS, 4 mM L-Glutamine (Biological industries Cat. No. 03-020-1A) and 1 mM Proline and 10 mcg/ml puromycin (Sigma Cat. No. P8833).

The puromycin was later removed in the cloning and subcloning steps.

The selected subclones showed a stable productivity of about 4 picogram/cell/24 hours. The highest PCD that was achieved was about 20 picogram/cell/24 hours, with a clone with the hGH signal peptide.

Example 5

Purification and N-Terminal Analysis of the Human FSH Beta Produced

The human FSH protein present in the supernatant of protoclons (from Examples 4) was purified by immunoaffinity chromatography, the subunits resolved by SDSPAGE, blotted into a PVDF membrane and subjected to amino-terminal amino acid sequence by Edman degradation (FIG. 4). It was found that the N-terminal of the human FSH beta subunit expressed by the protoclons having the signal peptide of hGH (88LP), have only the correct species of FSH beta with the following N-terminal amino acid sequence NSXELT (SEQ ID NO: 17). Moreover, not only the beta sub unit but, also the FSH alpha subunit in the same protoclon which was expressed with the endogenous signal peptide also show only the correct species of N-terminal sequence APDVQD ((SEQ ID NO: 18).

In contrast, FSH beta produced in a protoclon (91LP) with the cognate signal peptide exhibited about 27% truncated protein having the N-terminal amino acid sequence XELT (SEQ ID NO: 19) and the FSH alpha subunit expressed with the endogenous signal peptide in the same protoclon show 4% truncated FSH alpha subunit having the N-terminal amino acid sequence DVQD (SEQ ID NO: 20).

These results show that human FSH, comprising the alpha and beta subunits, is more homogeneously produced when the human GH signal peptide is employed instead of the cognate FSH beta subunit signal peptide.

Example 6

ELISA for FSH

Microtiter plates were coated with 3 µg/ml monoclonal antibody specific to FSH subunit beta (Cat 10-F25 Fitzgerald) in PBS and incubated overnight at 4° C. The plates were washed three times with washing buffer (PBS containing 0.05% of Tween 20) and blocked with 200 µl/well blocking buffer (PBS containing 0.2% BSA), for 1 hour at 37° C. After blocking, the plates were washed three times with washing buffer and 100 ml aliquots of samples, standard curve, and check samples were added to the plates and incubated for 60 min at 37° C. with shaking. After the incubation, the plates were washed three times with washing buffer, and 100 ml of second monoclonal antibody specific to FSH subunit alpha (Cat 61F20) conjugated with HRP were added to each well. The plates were incubated for 60 min at 37° C. with shaking. Following the incubation, the plates were washed again three times with washing buffer, and 100 ml of substrate solution (OPD Fast Sigma Code P-9187) were added to each well. After incubation of the plate for 20 min at room temperature without shaking the reaction was stopped by adding 50 µl/well of stop solution (4N HCl). The absorbance was measured at A492 nm in an ELISA reader. Standard solutions were prepared by serial dilutions of an r-hFSH reference to give a standard curve range from 0.625 to 10 ng/ml in assay buffer.

REFERENCES

Dinarello, C. A. (1996) "Biologic Basis for Interleukin-1 in Disease." Blood, 87, 2095-147.

Fanslow, W. C., Srinivasan, S., Paxton, R., Gibson, M. G., Spriggs, M. K., Armitage, R. J. (1994) "Structural characteristics of CD40 ligand that determine biological function." Semin Immunology, 5, 267-78.

Hartman, J. R., Nayak, D. P. and Fareed, G. C. (1982) "Human Influenza virus hemagglutinin is expressed in monkey cells using simian virus 40 vectors." Proc.Natl.Acad.Sci.USA, 79, 233-7.

Hollenbaugh, D., Grosmaire, L. S., Kullas, C. D., Chalupny, N. J., Braesch-Andersen, S., Noelle, R. J., Stamenkovic, I., Ledbetter, J. A., and Aruffo, A. (1992) "The human T cell antigen gp39, a member of the TNF gene family, is a ligand for the CD40 receptor: expression of a soluble form of gp39 with B cell co-stimulatory activity." EMBO J. 11, 4313-21.

Kozak, M. (1996) "Interpreting cDNA sequences: some insights from studies on translation." Mammalian Genome, 7, 563-74.

Kozak, M. (1999) "Initiation of translation in prokaryotes and eukaryotes." Gene, 234, 187-208.

Mazzei, G. J., Edgerton, M. D., Losberger, C., Lecoanet-Henchoz, S., Graber, P., Durandy, A., Gauchat, J. F., Bernard, A., Allet, B. and Bonnefoy, J. Y. (1995) "Recombinant Soluble Trimeric CD40 Ligand Is Biologically Active." J. Biol. Chem. 270, 7025-8.

Morris, A., Remmele, Jr., Klinke, R., Macduff, B. M., Fanslow, W. C. and Armitage, R. J. (1999) "Incorporation of an Isoleucine Zipper Motif Enhances the Biological Avtivity of Soluble CD40L (CD 154)." The journal of Biological Chemistry, 474, 418-23.

Nielsen, H., Engelbrecht, J., Brunak, S. and von Heijne, G. (1997) "Identification of prokaryotic and eukaryotic signal peptides and prediction of their cleavage sites." Protein Engineering, 10, 1-6.

Novick, D., Kim, S. H., Fantuzzi, G., Reznikov, L. L, Dinarello, C. A. and Rubinstein, M. (1999) "Interleukin-18 Binding Protein: A Novel Modulator of the Th1 Cytokine Response." Immunity 10, 127-136.

Pecceu, F., Dousset, P., Shire, D., Cavrois, E., Marchese, E., Ferrara, P., Kaghad, M., Dumont, X. and Lupker, J. (1991) "human interleukin 1b fused to the human growth hormone signal peptide is N-glycosilated and secretede by chinese hamster ovary cells." Gene, 97, 253-8.

Sakaguchi, M. (1997) "Eukaryotic protein secretion." Current Opinion in Biotechnology, 8, 595-601.

Selden, R. F., Howie, K. B., Rowe, M. E., Goodman, H. M. and Moore, D. D. (1986) "Human growth hormone as a reporter gene in regulation studies employing transient gene expression." Mol Cell Biol 6, 3173-9.

Zhao, J., Hyman, L., and Moore, C. (1999) "Formation of mRNA 3' ends in eukaryotes: mechanism, regulation and interrelationships with other steps in mRNA synthesis." Microbiology and Molecular Biology Reviews 63, 405-445.

The invention claimed is:

1. A method for improving the homogeneity of production of a recombinant follicle stimulating hormome (FSH) in a mammalian cell, comprising the step of substituting the endogenous signal peptide of at least one of the subunits of FSH with an amino acid sequence comprising the signal peptide of human growth hormone (hGH).

2. The method according to claim 1, wherein the endogenous signal peptide of one of the subunits is substituted with an amino acid sequence comprising the signal peptide of hGH.

3. The method according to claim 1 or 2, wherein the signal peptide of the beta subunit is substituted with an amino acid sequence comprising the signal peptide of the hGH.

4. The method according to claim 1 or 2, wherein the mammalian cell is selected from 3T3 cells, COS cells, human osteosarcoma cells, MRC-5 cells, BHK cells, VERO cells, CHO cells, rCHO-tPA cells, rCHO-Hep B Surface Antigen cells, HEK 293 cells, rHEK 293 cells, rC127-Hep B Surface Antigen cells, Normal Human fibroblast cells, Stroma cells, Hepatocyte cells, PER.C6 cells and human permanent amniocytic cells.

5. The method according to claim 4, wherein the mammalian cell is CHO.

6. An expression vector for improving homogeneity of production of a recombinant follicle stimulating hormone (FSH), comprising the DNA sequence of one or more subunits wherein the DNA sequence of the endogenous signal peptide of at least one subunit of FSH is replaced with the DNA encoding the sequence of the hGH signal peptide.

7. The expression vector according to claim 6, comprising the FSH beta subunit.

8. The expression vector according to claim 7, further comprising the DNA sequence of an alpha subunit.

9. A cell producing a recombinant follicle stimulating hormone, comprising a vector according to any one of claims 6, 7 or 8.

10. A cell producing a recombinant follicle stimulating hormone (FSH), comprising an expression vector according to claim 7, further comprising a vector encoding the sequence of the subunit alpha.

11. The cell according to claim 10, producing FSH in the range of 2 to 20 picogram/cell/24 hours.

12. The cell according to claim 10, producing FSH in the range of 2 to 10 picogram/cell/24 hours.

13. The cell according to claim 11, producing FSH in the range of 4 to 8 picogram/cell/24 hours.

14. The cell according to claim 12, producing FSH at about 4 picogram FSH/cell/24 hours.

15. The cell according to claim 9, capable of growing in serum free medium.

16. A method for producing a recombinant follicle stimulating hormone (FSH), comprising the step of growing a cell according to claim 9 and isolating the protein produced.

17. A method for producing a recombinant follicle stimulating hormone (FSH), comprising the step of growing a cell according to any one of claim 10, 11, 12, 13, or 14 and isolating the protein produced.

* * * * *